United States Patent [19]

Arnold, Jr. et al.

[11] Patent Number: 4,588,525

[45] Date of Patent: May 13, 1986

[54] PRODRUG COMPOUNDS FOR DERMAL APPLICATION

[75] Inventors: Lyle J. Arnold, Jr.; Jerome A. Streifel, both of San Diego, Calif.

[73] Assignee: Molecular Biosystems, Inc., San Diego, Calif.

[21] Appl. No.: 584,113

[22] Filed: Feb. 27, 1984

[51] Int. Cl.$^4$ ................................................ C07J 5/00
[52] U.S. Cl. .................................. 260/397.4; 544/125
[58] Field of Search .................... 260/397.4; 424/238; 544/125

[56] References Cited

U.S. PATENT DOCUMENTS

| | | | |
|---|---|---|---|
| 4,196,204 | 4/1980 | Petzold et al. | 260/397.4 |
| 4,224,320 | 9/1980 | Dahl et al. | 260/397.4 |
| 4,258,052 | 3/1981 | Yu et al. | 424/266 |
| 4,329,294 | 5/1982 | McCombs | 260/397.4 |

Primary Examiner—Elbert L. Roberts

[57] ABSTRACT

Prodrug compounds for dermal application of topical medicaments, such as 6-aminonicotinamide for treatment of psoriasis, are linked by an enzyme cleavable group to a carrier side chain, such as succinyl piperidate or morpholidate. The neutral lipophilic compounds are rapidly absorbed into the epithelial cells where they are enzymatically cleaved to release the active drug in an ionic form which is retained within the cells.

12 Claims, No Drawings

PRODRUG COMPOUNDS FOR DERMAL APPLICATION

FIELD OF INVENTION, BACKGROUND, AND PRIOR ART

The field of this invention is topical drugs for treating disease conditions of the skin or mucous membranes such as drugs for the treatment of psoriasis. The invention is particularly concerned with topical drugs which are administered in the form of prodrug compounds which are bioconvertible to the active drugs by enzymatic action.

In designing dermal targeting systems the improved absorption of the drug may require that its character be modified to an electronically neutral, non-ionic form so that it passes through the cell walls more readily. Further, lipophilic forms of such drugs are in general more readily absorbed into the dermal or epidermal cells. When the active drug itself is a charged moiety in aqueous solution and/or is inadequately lipophilic, it has been proposed to modify the drug to a prodrug form having these characteristics. For effective action after absorption, however, such prodrugs must be converted to the active drug within the target cells, but very little is known about the required chemical structure for such topical bioavailability.

Another problem which is encountered with respect to topical drugs is that the active form may have a serious toxic side effect if present in the circulatory system in significant concentrations. For example, it is known that the drug 6-aminonicotinamide (6-AN) is more effective against psoriasis than methotrexate but that it requires greater care in use. It has been shown that unless topical applications of 6-AN are accompanied by oral nicotinamide, a central nervous system toxicity (CNS) may result (Zackheim (1975) *Arch. of Derm.* 111: 880–882; and Zackheim (1978) *Arch. of Derm.* 114: 1632–1638.). 6-AN has also been shown to have anti-cancer activity but its use is questionable due to the CNS side effects (Ross (1967) *Biochemical Pharm.* 16: 675–680; Miyasaka et al (1975) *J. Pharm. Soc. Japan* 95: 547–551.). For treatment of psoriasis or skin cancer, it would be desirable to administer 6-AN in the form of a prodrug to permit uptake by cells while reducing its systemic toxicity.

U.S. Pat. No. 4,258,052 discloses various chemical analogues of 6-AN including substituents on the 6-amino group. In some of these the amino group of the side chain has been converted to an amide group which connects to an aliphatic group terminating in an ester group. For example, such compounds include the methyl and ethyl esters of 6-succinylamino nicotinamide.

SUMMARY OF INVENTION

The novel compounds of the present invention provide a means for preparing prodrugs useful in the dermal application of topical medicaments such as 6-aminonicotinamide, methotrexate, cortisone and related compounds for treatment of psoriasis and other skin conditions. These prodrugs are models for other compounds having corresponding carrier side chains to be used for treating disease conditions of the epithelium wherein the drug acts by absorption into the epithelial cells.

The carrier side chain linkage to the topical drug can be attached at the site of a hydroxyl, amine, or carboxyl group of the parent drug, providing such groups are available for ester or amide linkage from formation. In the prodrug form, these topical drugs are linked to the carrier side chain through an amide, formed from the parent amine group, or to an ester formed from a parent hydroxyl or carboxyl group. The linking group connects to an alkyl group having a terminal amide group.

The resulting compounds are usually more lipophilic, and subject to cleavage by cellular enzymes such as the esterases and/or peptidases. For example, if the terminal amide group is enzymatically cleaved, the resulting compound will have a negative charge, which will promote cell retention after absorption in its neutral lipophilic form. Further enzymatic cleavage of the amide amino or ester linking group will convert the drug to its active form which may be ionic and relatively less lipophilic. For promoting rapid absorption into the target cells, lower doses can be topically applied thereby reducing the amount of the drugs being transported to other parts of the body, or, on entering the circulatory system, the drugs may be of reduced toxicity or in a form which is rapidly eliminated from the body.

Evidence exists for the cleavage of ester and amide linkages with the skin and body. For example, Higuchi and co-workers have shown that various esters of vidarabine can be absorbed and bioconverted to an active drug in hair-less mouse skin (*J. Pharm. Sci.* 69: 772–775 (1980)). In addition, Banerjec and Amidon have found that various amides and esters of aspirin can be cleaved by carboxypeptidase to free aspirin (*J. Pharm. Sci.* 70: 1307–1309 (1981)).

DETAILED DISCLOSURE

The topical prodrug compounds coming within the generic concept of the present invention can be represented by the following structural formulae:

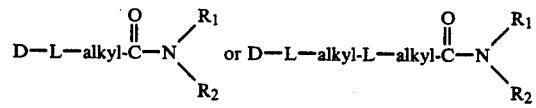

In the above formula the letter "D" represents the topical drug in its active form. The letter "L" represents an enzyme cleavable linking group. In the preferred embodiments, the linking groups (L) are either an amido group or an ester group. The alkyl group is preferably a relatively short chain alkyl group, such as $C_1$-$C_5$ alkyl. Typical alkyl groups are ethyl, propyl, and butyl.

In the above formula, the letters C, O, and N have their usual meanings, representing respectively atoms of carbon, oxygen, and nitrogen. The nitrogen (N) is either a nitrogen in a heterocyclic ring, in which case $R_1$ and $R_2$ are combined in the ring, or $R_1$ and $R_2$ are separate side chains. For example, $R_1$ and $R_2$ may be $C_1$-$C_6$ alkyl. Methyl or ethyl groups are believed to be preferred. Either $R_1$ or $R_2$ may be hydrogen (H) when the other R group is an alkyl group of the kind described. When N, $R_1$ and $R_2$, are components of a heterocyclic ring, the ring may contain from 3 to 5 carbons and may also include other atoms such as oxygen and nitrogen, the ring being either 5 or 6 membered. In particular, morpholine and piperidine groups are preferred.

In addition to 6-aminonicotinamide (6-AN) and methotrexate, a wide variety of other topical drugs can be prepared in prodrug form. The carrier side chains of the kind described can be readily bonded to the drugs through hydroxyl, amine, or carboxyl groups of the parent compound. As long as the parent compound contains at least one of these groups which is available for ester or amide linkage, the prodrugs can be readily prepared by known chemical synthesis procedures. Such dermally applicable drugs include the following:

| Antiviral | Antibacterial |
|---|---|
| trifluridine | chloramphenicol |
| cytosine arabinoside | neomycin |
| | erthromycin |
| | gentamicin |
| | mafenide |
| | penicillin and many of its analogues |
| | streptomycin |
| | sulfanilamide and other sulfa drugs |
| | tetracycline |

| Antineoplastic | Anti-inflammatory |
|---|---|
| doxorubicin | prednisolone |
| | dexamethasone |
| | fluorcinonide |
| | algestone |
| | fludrocortisone |
| | hydrocortisone |

| Hormones | Anesthetic |
|---|---|
| estradiol | proparacaine |
| estriol | benoxinate |
| | bethoxycaine |
| | biphenamine |
| | procaine |
| | thiocaine |

| Other |
|---|
| hydroxyamphetamine |
| phenylephrine |
| betamethasone |
| fluocortolone |
| cortisone |
| epinephrine |
| isoproterenol |
| phenylethanolamine |
| prednisone |
| prostaglandins $E_1$, $E_2$, $F_2$ |
| Vitamin A |

For treatment of psoriasis, the preferred drug is 6-aminonicotinamide (6-AN). A subclass of psoriasis prodrugs is represented by the following formulae:

In the above formulae "D" is 6-AN, the alkyl groups contains from 1 to 5 carbons, such as preferably 2 to 4 carbons, the R group represents a heterocyclic group containing the nitrogen of the terminal amide group and L is an amide or ester group. Preferred R groups are morpholine and piperidine.

When the topical drug is retinoic acid or 17α-hydroxyprogesterone, the linking group (L) is preferably an ester group. In desirable embodiments of such ester linked drugs, the alkyl group may be ethyl or butyl, and the terminal amide in the form of a morpholidate or piperidate group. Preferred specific compounds for anti-psoriasis use include 6-aminonicotinamide-$N^6$-succinylpiperidate and 6-aminonicotinamide-$N^6$-succinylmorpholidate. Corresponding analogues of other topical drugs are also believed to be particularly desirable forms.

In preparing the prodrugs, the entire carrier moiety can be synthesized first and then coupled to the drug using appropriate condensing chemistry. In the alternative, the carrier moiety can be built on to the topical drug by first adding the aliphatic portion linked through an ester or amide group, and thereafter converting the terminal group, such as a terminal carboxyl group to a terminal primary or secondary amide.

A large number of convenient chemical reactions may be used to synthesize the carrier moiety prior to attaching it to the desired drug. These include the reaction of primary or secondary amines with: (1) cyclic and linear esters; (2) carboxyl groups in the presence of appropriate condensing or activating agents such as carbodiimide, thionyl chloride, $CaCl_2$, etc.; (3) cyclic anhydrides; (4) acid halides such as acid chlorides and acid bromides; and (5) amides capable of undergoing exchange reactions with primary and secondary amines. The portion of the carrier moiety distal to the site of amide formation may be carboxyl, hydroxyl, or amino. Depending upon the chemistry employed, however, it may be necessary to use protecting groups to prevent reactions at these sites. This is particularly true for amide and hydroxyl groups. For a discussion of such protecting groups see Reagents for Organic Synthesis (ed. F. L. Fieser and M. Fieser) Vol. 1–10, Wiley, NY 1967–1982.

Once the carrier moiety has been synthesized it may be attached to the drug using standard condensing chemistry. The chemical method used is dependent upon the functionalities present on the drug and carrier moiety. The formation of an ester linkage between the drug and carrier moiety requires that the drug or chemical agent contains a carboxyl or hydroxyl functionality and conversely that the carrier moiety contains a hydroxyl or carboxyl moiety. Alternatively, in the formation of an amide linkage the drug or chemical agent may contain a carboxy or amino group and the carrier may contain an amino or carboxy group respectively.

Chemical methods favor the activation of the carboxyl moiety in the formation of ester and amide linkages. As a result, either the drug or the carrier moiety is activated depending upon which one of them contains the carboxyl moiety desired for participation in the ester or amide linkage. When interfering functional groups are absent activation may take place with both the drug and carrier moieties present. If interfering functional groups are present, it may be necessary to protect such groups (see Reagents for Organic Synthesis, ibid) or sufficient to preactivate the carboxyl group in the absence of its ester or amide bond forming partner. Activation of the carboxyl group may be achieved by: (1) conversion to active esters such as N-hydroxysuccinimide active esters using carbodiimides; (2) conversion to active intermediates directly with carbodiimides, (3) conversion to acid chlorides using thionyl chloride; and (4) conversion to anhydrides using calcium chloride or other dehydrating agents. Once the carboxyl group is activated it may be reacted with the amine or hydroxyl containing component to form the desired ester or amide product.

Alternatively similar chemical methods may be employed essentially in reverse to synthetically build the carrier moiety onto the drug. Drugs which possess amine or hydroxyl groups at the site of carrier attachment may be reacted with anhydrides, acid halides, esters (particularly active ester), or acid functionalities in the presence of a carbodiimide or other condensing agent such as calcium chloride. These reactions attach the first portion of the carrier moiety to the drug. At this point, the free end of the developing carrier moiety may possess an acid halide functionality, an ester or active ester moiety, or a free carboxylate group. The terminal amide may be formed by reacting a primary or secondary amine directly with the acid halides or ester functions. When the terminal group is carboxyl it may be converted to an active ester using carbodiimides or other condensing agents and then reacted with the primary or secondary amines to form the terminal amide. Alternatively, terminal carboxyl groups may be reacted directly with primary or secondary amines to form amides in the presence of a carbodiimide or other condensing agents.

Similarly, when the drug contains a carboxyl group for carrier attachment it may be converted to an ester, to an acid chloride, or activated directly with a carbodiimide or other condensing agent. Either simultaneous or subsequent addition of an amine or hydroxyl group containing intermediate carrier component will produce an amide or ester linkage respectively. The terminal amide is then formed as described above using thionyl chloride, carbodiimide or other condensing agents, and a primary or secondary amine.

In some instances it is desirable to incorporate additional ester or amide cleavage sites. This can be readily done by repeating one of the steps described above, to further elongate the carrier. de The prodrug compounds coming within the generic concept of the present invention are further illustrated by the following examples.

EXAMPLE I

6-Aminonicotinamide-$N^6$-succinyl piperidate was prepared as follows: 5 g (0.036 mole) of 6-aminonicotinamide and 5.75 g (0.057 mole) of succinic anhydride was dissolved in 50 mls of anhydrous dimethyl sulfoxide. The mixture was heated with stirring at 100° C. for four hours. The temperature was then lowered to 70° C. and allowed to incubate overnight. The heat was then removed and the mixture stood for two days at room temperature. Upon the addition of 50 mls of water at 0° C., a white precipitate formed. The precipitate was washed several times with water at 0° C. The precipitate was then placed in 30 ml dioxane and lyophillized. The crude 6-aminonicotinamide-$N^6$-succinic acid was then recrystallized from ethanol and its structure was confirmed by $^1$H-NMR. Upon heating, the compound decomposes at 270°–275°.

1 g (0.0043 mole) 6-aminonicotinamide-$N^6$-succinic acid, 0.88 g (0.0065 mole) p-nitrophenol and 1.77 g (0.0086 mole) of dicyclohexyl carbodiimide was dissolved with gentle heating in 250 ml dry pyridine. After stirring overnight, 4.3 g (0.05 moles) piperidine was added and stirring continued for four hours at room temperature. 250 mls of water were then added followed by four extractions with 500 ml hexane. The aqueous phase was then rotoevaporated to dryness. The material remaining was dissolved in a small volume of absolute methanol and dried onto 5 g silica gel. This silica gel absorption process was repeated three times from methanol and twice from ether. The silica gel with the absorbed crude amide was layered on to the top of a silica gel column which was previously equilibrated with methanol: chloroform (1:9, v/v). The column was then eluted with methanol: chloroform (1:9, v/v). Those fractions which showed material with an rf=0.32 (using silica gel TLC plates and the same solvent) were pooled, evaporated and rechromatographed in the same manner in order to remove the last traces of p-nitrophenol. $^1$H-NMR was used to confirm the structure of the amide product.

EXAMPLE II

6-Aminonicotinamide-$N^6$-succinylmorpholidate was prepared by the procedure described in Example I except that 5 g (0.059 moles) morpholine was used instead of piperidine in the synthesis of the amide. Those fractions with an rf=0.25 were collected and rechromatographed.

EXAMPLE III

The compounds of Examples I and II were tested for prodrug activity, and the level of activity was compared with the parent compound 6-aminonicotinamide, and with ester derivatives thereof as disclosed in U.S. Pat. No. 4,258,052; namely, alkyl esters of 6-succinyl amino nicotinamide. The structure of the compounds were confirmed by using $^1$H-NMR at 360 MHZ. The test procedure and results are described below.

Test Procedure

Drugs were evaluated by their ability to inhibit the growth of human lung fibroblasts in culture. Human lung fibroblasts were grown in Eagle's Minimal Essential Media (EMEM) which contained 10% fetal calf serum, 1X non-essential amino acids, and 250 units penicillin and 250 μg streptomycin/ml. Stock cultures of the cells were grown on 100 mm culture plates. For testing purposes, cells were removed from the stock plates with 3 mls trypsin/versene and after appropriate dilution in the culture medium were plated onto 35 mm dishes. Typically, cells were subcultured at $10^4$ cells/35 mm dish in 1.5 mls of medium and allowed to attach for 24 hours before the addition of drugs. Triplicate plates were treated with drugs over a wide concentration range. In some cases, it was necessary to dissolve stock solutions of the drugs with 50% ethanol. In such cases, appropriate controls were included to assure that the ethanol had no adverse effects. In all cases, untreated triplicate control plates were employed in order to determine the cell population at the time of drug addition and at the time of experiment completion (usual 3–4 days). The number of cells on the test and control plates was determined by first removing the medium by aspiration followed by gentle washing with 1 ml phosphate buffered saline. Trypsin/versene (0.5 ml) was then added and the plates incubated at 37° C. for up to 15 minutes or until the cells became detached. One milliliter of EMEM which contained 1X non-essential amino acids was then added in order to neutralize the action of trypsin. The cells were then diluted into ISOTON II (Curtin Matheson Scientific, Houston, Tex.) and counted on a Coulter counter (Coulter Electronics, Hialeah, Fla.) according to the Coulter counter owner's manual. The $ID_{50}$ was determined by relating the concentration of drug to the point where the cells were exhibited in their growth by 50%.

Test Results

The results of the tests are summarized below in Table A:

TABLE A

| Chemical Name | $ID_{50}$ |
| --- | --- |
| 6-Aminonicotinamide | $2 \times 10^{-6}$ M |
| 6-Aminonicotinamide-$N^6$—succinic acid | $2 \times 10^{-3}$ M |
| 6-Aminonicotinamide-$N^6$—succinyl piperidate | $1-2 \times 10^{-6}$ M |
| 6-Aminonicotinamide-$N^6$—succinyl morpholidate | $1-2 \times 10^{-6}$ M |
| 6-Aminonicotinamide-$N^6$—succinate methyl ester | $2 \times 10^{-5}$ M |
| 6-Aminonicotinamide-$N^6$—succinate ethyl ester | $5 \times 10^{-6}$ M |
| 6-Aminonicotinamide-$N^6$—succinate butyl ester | $2 \times 10^{-5}$ M |
| 6-Aminonicotinamide-$N^6$—succinate hexyl ester | $2 \times 10^{-5}$ M |
| 6-Aminonicotinamide-$N^6$—apidic acid ethyl ester | $3 \times 10^{-5}$ M |
| $N^6$—heptanoyl-6-aminonicotinamide | $2 \times 10^{-5}$ M |

Interpretation

Table A indicates that 6-aminonicotinamide-$N^6$-succinylpiperidate and 6-aminonicotinamide-$N^6$-succinylmorpholidate are readily converted by cellular enzymes to an active 6-aminonicotinamide which is responsible for the inhibition of cell growth. Such conversion appears to be more efficient for these two analogues than it is for any of the other alkyl or ester analogues. Significantly, the inactivity of 6-aminonicotinamide-$N^6$-succinate indicates that cleavage of the terminal amides of corresponding analogues would generate a substance (6-aminonicotinamide succinate) which is essentially inactive. Such cleavages might be exploited to retain local activity but to eliminate systemic toxicity.

EXAMPLE IV

N(4-hydroxylbutyryl)morpholidate retinoic acid ester can be prepared by the following procedure: The carrier moiety is synthesized first and then attached to retinoic acid using dicyclohexylcarbodiimide. 8.6 g (0.1 mole) of γ-butryolactone is added to 8.7 g (0.1 mole) morpholine in 100 ml of anhydrous benzene. This mixture is then gently refluxed overnight. The benzene is removed in vacuo and the crude amide recrystalized from an appropriate solvent such as ethanol. The structure of the resulting N-(4-ydroxybutyryl)morpholidate is verified using $^1$H-NMR.

To 100 mls of anhydrous pyridine is added 3 g (0.01 mole) retinoic acid, 8.6 g (0.05 moles) N(4-hydroxybutyryl)morpholidate, 1.2 g (0.01 moles) N-hydroxysuccinimide) as a catalyst, and 4 g (0.02 moles) dicyclohexylcarbodiimide. The mixture is then heated overnight in the dark at 50° C. with stirring. After evaporation of the pyridine the product ester is purified on a silica gel column using a linear gradient of $CHCl_3$-methanol as the eluting solvent. The eluted fractions have a UV absorption in the region of 350 nm characteristic of retinoids are collected. Those fractions corresponding to retinoid esters by virtue of their migration patterns on silica gel TLC plates are pooled and the solvent removed in vacuo. The structure of the product is confirmed using $^1$H-NMR and U.V. spectroscopy.

EXAMPLE V

N(4-hydroxybutyryl)diisopropylamine retinoic acid ester can be prepared by the following procedure. 8.6 g (0.1 mole) of γ-butyrolactone is added to 10.1 g (0.1 mole) of diisopropylamine in anhydrous benzene and refluxed overnight. The remainder of the synthesis follows the same steps as Example IV.

EXAMPLE VI

N(6-aminocaproyl)morpholidate retinoic acid amide can be prepared by the following procedure. 3 g (0.01 mole) of retinoic acid is dissolved in 30 mls of anhydrous pyridine followed by the addition of 2 g (0.01 mole) dicyclohexycarbodiimide and 1.35 g (0.01 mole), 1-hydroxybenzotriazole. This mixture is stirred overnight in the dark at 50° C. One equivalent of 6-aminocaproic acid is then added (1.3 g, 0.01 mole) and the reaction continued for an additional 18 hours at 50° C.

Without purifying the intermediate, an additional 20 mls of anhydrous pyridine containing 2 g (0.01 mole) dicyclohexylcarbodiimide and 0.87 g (0.01 mole) morphiline are added to the reaction mixture. After sitting 48 hours in the dark at room temperature, the solvent pyridine is removed in vacuo. The desired non-charged amide product is separated (as described in Example I) from charged species which contain the 350 n.m. absorbing retinoid material. Final verification of structure is made using $^1$H-NMR and ultraviolet spectroscopy.

EXAMPLE VII

17α-Hydroxyprogesterone-17-succinyl piperidate can be prepared by the following procedure. 17α-hydroxy- progesterone-17-hemisuccinate is purchased from Research Plus, Inc. Bayonne, N.J. 4 g(0.01 mole) of 17α-hydroxyprogesterone-17-hemisuccinate is dissolved in 50 mls of anhydrous pyridine which contains 2.6 g (0.02 mole) dicyclohexylcarbodiimide and 0.85 g (0.01 mole) piperidine. This mixture is then allowed to incubate for 72 hours with stirring at room temperature. The pyridine is removed in vacuo and the residual material is purified using silica gel with a mixture of chloroform/methanol as the eluting solvent.

The optimal proportions of chloroform and methanol to be used are predetermined using silica gel TLC plates. The solvent mixture which gives optimal separations of parent compounds and the amide product is used.

After elution from the silica gel column, those fractions containing the progesterone derivative are identified by their 240 nm absorption. These fractions are evaporated and the ones containing the amide are verified by their $^1$H-NMR spectra.

EXAMPLE VIII (6-aminonicotinamide-$N^6$-succinate (N-(4-hydroxybutyryl)-morpholidate) ester is prepared as follows: N-(4-hydroxybutyryl) morpholidate is first prepared and subsequently condensed with 6-aminonicotinamide-$N^6$-succinate to form an ester linkage. 8.6 g (0.1 mole) of γ-butryolactone is added to 8.7 g (0.1 mole) morpholine in 100 ml of anhydrous benzene and the mixture gently refluxed overnight. The benzene is removed in vacuo and the crude amide recrystalized from ethanol. The structure of the resulting N-(4-hydroxybutyryl)morpholidate is verified using $^1$H-NMR.

6-aminonicotinamide-$N^6$-succinic acid is prepared as described in Example I.

2.3 g (0.01 mole) 6-aminonicotinamide-$N^6$-succinic acid, 1.2 g (0.01 mole) N-hydroxysuccinimide, 4.3 g (0.025 moles) N-(4-hydroxybutyryl)morpholidate and 4 g (0.02 moles) dicyclohexyl carbodiimide is suspended in 100 mls of anhydrous pyridine. This mixture is heated overnight at 50° C. with stirring. The pyridine is evaporated in vacuo and the crude ester product dissolved in absolute methanol leaving behind the carbodiimide urea. The crude product is dired onto 5 g silica gel and placed on the top of a silica gel column. The column is then eluted with a linear gradient of chloroform-methanol. Those fractions showing the characteristic 254 nm absorption of 6-aminonicotinamide derivatives are pooled and the solvent evaporated. This column procedure is repeated as necessary in order to obtain a highly pure product. The structure of the product is confirmed using $^1$H-NMR.

We claim:

1. Prodrug compounds for dermal application represented by the following formulae:

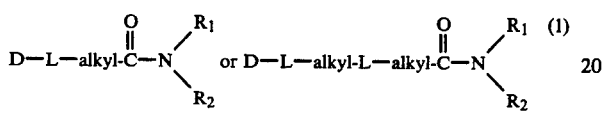

wherein D is 6-aminonicotinamide and L is an amide group, said alkyl groups containing from 1 to 5 carbons, said C, O and N representing respectively carbon, oxygen and nitrogen, and $R_1$ and $R_2$ are selected from (i) alkyl groups of 1 to 6 carbons, (ii) hydrogen when the other of the R group is alkyl, or (iii) combined to form a heterocyclic ring with the N contained therein and including 3 to 5 carbons.

2. The prodrug compounds of claim 1 in which the $R_1$ and $R_2$ are compounds to form a heterocyclic ring selected from the class consisting of morpholine and piperidine.

3. The prodrug compounds for treatment of psoriasis represented by the following formula:

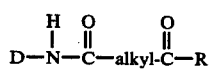

wherein D is 6-aminonicotinamide, the alkyl group contains from 1 to 5 carbons, and R is selected from the class consisting of morpholino and piperidinyl.

4. The prodrug compounds of claim 3 in which alkyl is ethyl.

5. 6-Aminonicotinamide-N$^6$-succinylpiperidate.

6. 6-Aminonicotinamide-N$^6$-succinylmorpholidate.

7. N(4-hydroxylbutyrl) morpholidate retinoic acid ester.

8. N(4-hydroxybutyrl) diisopropylamine retinoic acid ester.

9. N(6-aminocaproyl) morpholidate retinoic acid amide.

10. 17α-Hydroxyprogesterone-17-succinyl piperidate.

11. (6-Aminonicotinamide-N$^6$-succinate (N-(4-hydroxybutyryl)-morpholidate) ester.

12. Prodrug compounds for dermal application represented by the following formulae:

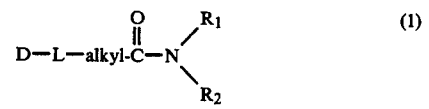

or

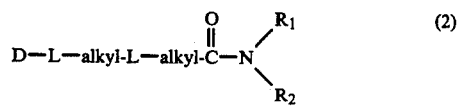

wherein D is a topical drug selected from the group consisting of 6-aminonicotinamide for which L is an amide, retinoic acid for which L is an ester group, and 17α-hydroxyprogesterone for which L is an ester group, said alkyl groups containing from 1 to 5 carbons, said C, O and N representing respectively carbon, oxygen and nitrogen, and $R_1$ and $R_2$ are selected from (i) alkyl groups of 1 to 6 carbons, (ii) hydrogen when the other of the R group is alkyl, or (iii) combined to form a heterocyclic ring with the N contained therein and including 3 to 5 carbons.

* * * * *